United States Patent [19]

Brown, Jr. et al.

[11] 3,952,053

[45] Apr. 20, 1976

[54] METHOD FOR RECOVERING TEREPHTHALIC ACID AND ETHYLENE GLYCOL FROM POLYESTER MATERIALS

[75] Inventors: George E. Brown, Jr., Cincinnati; Richard C. O'Brien, Dayton, both of Ohio

[73] Assignee: Safetech, Inc., Cincinnati, Ohio

[22] Filed: Feb. 26, 1974

[21] Appl. No.: 446,014

[52] U.S. Cl. .................................................. 260/525
[51] Int. Cl.² .......................................... C07C 51/42
[58] Field of Search ......................... 260/525, 515 P

[56] References Cited
UNITED STATES PATENTS

| | | | |
|---|---|---|---|
| 3,098,046 | 7/1963 | Siggel et al. | 260/2.3 |
| 3,108,082 | 10/1963 | Riehl et al. | 260/2.3 |
| 3,120,561 | 2/1964 | Chambret | 260/525 |
| 3,222,299 | 12/1965 | MacDowell | 260/2.3 |
| 3,240,804 | 3/1966 | Knobloch et al. | 260/525 |
| 3,317,519 | 5/1967 | Lazarus et al. | 260/239.3 |
| 3,388,156 | 6/1968 | Sakurai et al. | 260/525 |
| 3,488,298 | 1/1970 | Barkley et al. | 260/2.3 |
| 3,594,414 | 7/1971 | Katzschmann | 260/515 R |

OTHER PUBLICATIONS

Chmiel et al. *J. Am. Chem. Soc.* 78 3326 (1956).

*Primary Examiner*—Anton H. Sutto
*Attorney, Agent, or Firm*—Wood, Herron & Evans

[57] ABSTRACT

The process described herein relates to a process for recovering terephthalic acid and ethylene glycol from polyester materials produced from terephthalic acid and ethylene glycol.

9 Claims, 1 Drawing Figure

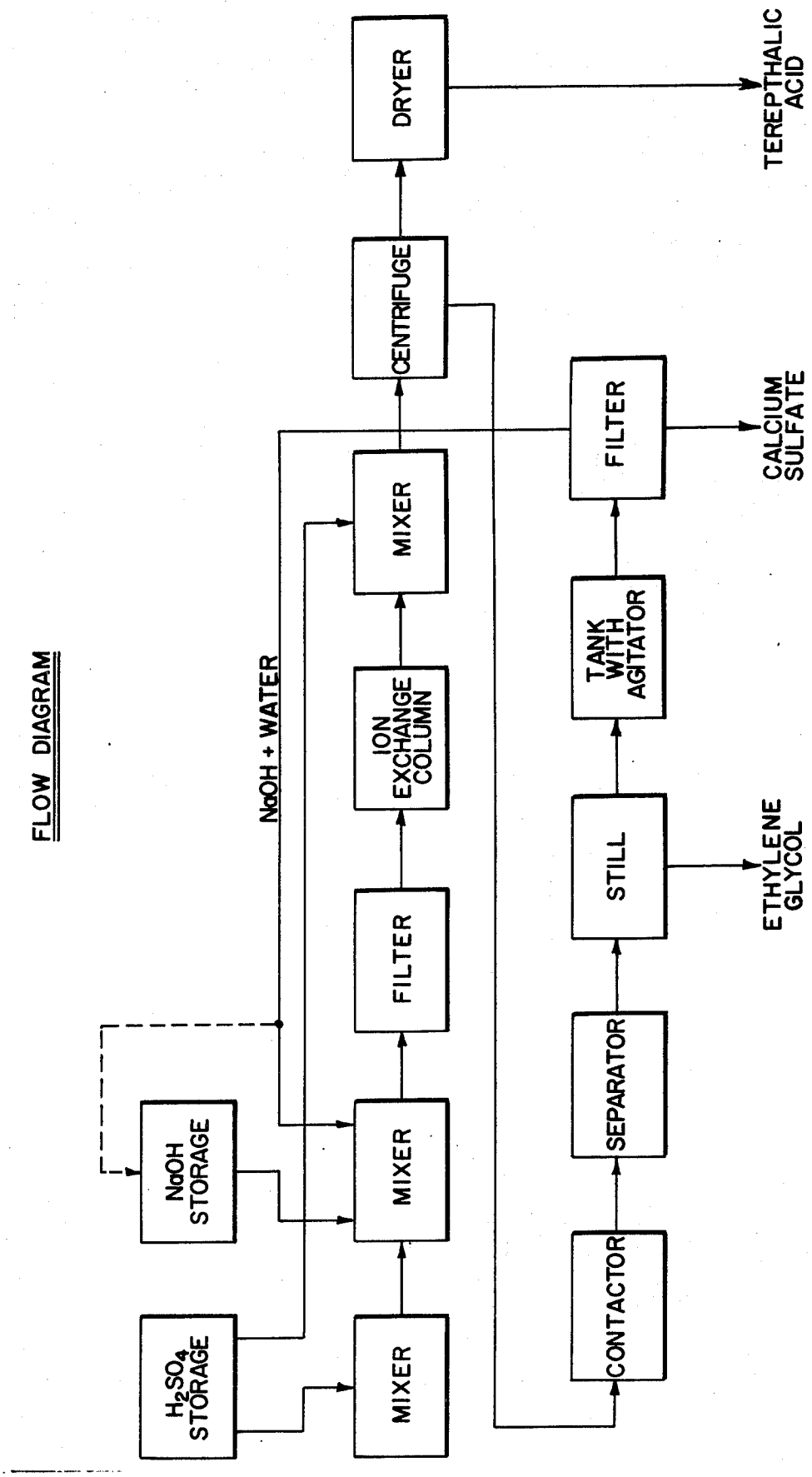

METHOD FOR RECOVERING TEREPHTHALIC ACID AND ETHYLENE GLYCOL FROM POLYESTER MATERIALS

BACKGROUND OF THE INVENTION

World-wide synthetic fiber production has expanded greatly in recent years and today millions of pounds of synthetic fibers are manufactured annually. A substantial and increasing portion of such production consists of polyester fibers. Such polyester fibers are frequently manufactured from terephthalic acid and ethylene glycol.

In the manufacture of fabrics and wearing apparel from terephthalic acid-ethylene glycol type polyester fibers large quantities of scrap and cuttings are produced. In fact, there are believed to be several hundred million pounds of such scrap produced annually. Heretofore such scrap has either been destroyed or sold as scrap for various secondary or incidental uses. The destruction of such scrap, as for example, by incinerating or dumping, has contributed to the world's environmental problems.

Final products other than fibers are also manufactured from polyester polymers and in such production large quantities of scrap are also generated. And, as in the case of the fabric scrap, there exists the problem of disposal and a need for recovering for reuse the components of the polyester material.

In addition to the need to reduce environmental contamination there also exists a need for terephthalic acid and ethylene glycol. In fact, with the increasing demand for such materials and the reduced supplies of feedstocks to produce them, there is a current shortage of them.

In U.S. Pat. No. 3,317,519 there is disclosed a process, primarily directed to recovering caprolactam from processes polyamidepolyester fabric, where terephthalic acid is also recovered. Other porcesses for recovering terephthalic acid from other materials are also described in the following U.S. Pat. Nos. 3,098,046, 3,108,082, 3,120,561, 3,222,299, 3,488,299, and 3,594,414.

Even though there has existed a need in the art to recover terephthalic acid from polyester materials, no one has devised a process which will do so without the need to use exotic chemicals, elevated temperatures, high pressures and/or expensive equipment. Moreover, no process is known whereby the recovery is achieved quickly and with terephthalic acid yields approaching 100% of theoretical maximum yield. This invention is, therefore, directed to providing such a process.

An important objective of this invention is to recover terephthalic acid from polyester materials without the use of elevated temperatures and pressures. Another important objective has been to provide such a process that economically recovers terephthalic acid. A still further objective is to recover not only terephthalic acid from a terephthalic acid-ethylene glycol polyester, but to recover the ethylene glycol as well. And, lastly, a principal objective has been to provide an ecologically "clean" process for recovering the terephthalic acid.

SUMMARY OF THE INVENTION

It has been empirically discovered that terephthalic acid may be quickly, i.e., in about 3–5 minutes, recovered from polyester scrap materials produced in part from terephthalic acid monomer, by first subjecting the polyester to concentrated (at least 87%) sulfuric acid, preferably heated to 140°–200° F. Then, if decolorizing and depigmentation are necessary, the mixture is added to a water-alkali solution. After removal of the pigments and dyes the mixture is added to a water-acid solution and terephthalic acid is precipitated. If a terephthalic acidethylene glycol polymer is the starting material, then the ethylene glycol may be recovered. Such is achieved by a solvent extraction step.

It is believed that the mechanism of this reaction follows a very simple train of steps. While we do not wish to be bound by this theory, its explanation may be of some use in understanding the process. First, the sulfuric acid reacts with the polyester chain by adding to the double bond oxygen of the ester linkage as follows.

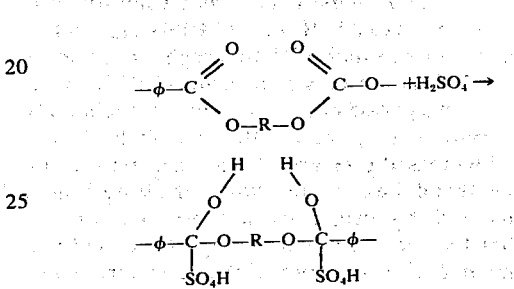

Second, when this compound is added to water, the water reforms the sulfuric acid and substitutes an hydroxol group to the chain as follows.

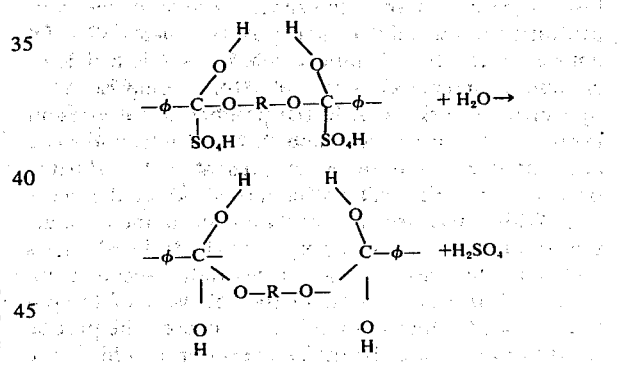

Third, the presence of two hydroxol groups on the same carbon, being chemically unstable, undergoes spontaneous rearrangement and splitting as follows.

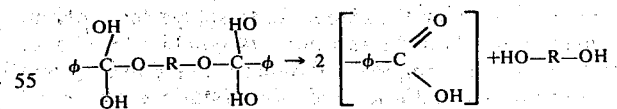

DESCRIPTION OF THE PREFERRED EMBODIMENTS

In the present process terephthalic acid may be recovered from various polyester materials. As used hereinafter the phrase "polyester material" is specifically meant to identify polyester polymers formed from terephthalic acid or dimethyl terephthalate. An important class of such polyester materials, i.e., polyethylene terephthalate, is formed from ethylene glycol and terephthalic acid or dimethyl terephthalate. Such materials are currently being produced and sold in substantial quantities, some under the trademarks "Dacron", "Trevira" and "Teryline". Processes for manufacturing polyesters of this type are well known in the art. See, for example, U.S. Pat. Nos. 3,118,739, 2,933,476 and 2,758,915.

The polyester material may comprise fabric scraps produced during cloth making operations. Such will ordinarily include various dyes and pigments. With such materials a procedure is provided whereby the dyes and pigments are removed so as to produce a colorless product of "fiber grade" quality.

In practicing the present process, concentrated sulfuric acid must be utilized. It has been unexpectedly determined that unless concentrated sulfuric acid is used the process in inoperative or, while not totally inoperative, takes so long as to be impracticable. More particularly, it has been discovered that a sulfuric acid concentration of at least 87%, i.e., 87% by weight sulfuric acid and no more than 13% by weight water, must be employed if the process is to achieve the desired recovery within a period of several minutes at relatively low temperatures, i.e., about 140° to 200° F., in the absence of increased pressures. It has been empirically determined that if the concentration of the sulfuric acid is less than 87% by weight and not less than 80% by weight that the recovery of the terephthalic acid will take hours at 212° F. or more. If the concentration of the sulfuric acid is less than 80% by weight then the recovery of the terephthalic acid will take a minimum of several days, a point in concentration being reached where no recovery is achieved. Therefore, in order to recover the terephthalic acid within several minutes at low temperatures and atmospheric pressure, the concentration of the sulfuric acid must be at least 87%. Of course, concentrated sulfuric acid is a staple article of commerce and in its concentrated form comprises 95% by weight sulfuric acid. In the practice of the present invention it is desirable to use this concentration since any minor amounts of water present in the starting polyester material will not adversely affect the reaction. While there are general statements in the prior art that sulfuric acid "decomposes" or "hydrolizes" esters and polyesters no one has successfully used concentrated sulfuric acid to effect the recovery of terephthalic acid. Neither has anyone discovered the precise conditions that must be utilized in order to achieve the recovery of almost pure terephthalic acid in an amount approaching that which has originally present in the polyester material treated.

It has been determined that the amount of sulfuric acid employed should be at least equal to and preferably greater than the amount of the polyester material. In other words, and referring to the combined weight of the materials comprising the mixture of polyester and concentrated sulfuric acid, the sulfuric acid should comprise at least 50% by weight of said mixture and preferably about 60% by weight of such mixture. If the amount of sulfuric acid is below 50% by weight, the recovery sought is not achieved.

In treating the polyester material with the concentrated sulfuric acid it is preferable to heat the sulfuric acid to a temperature of between about 140° and 200° F. before the polyester material is added thereto. While lower temperatures may be employed, the reaction proceeds at a reduced rate and the resultant material is very viscous. For reasons not entirely understood, the viscosity is substantially reduced when the reaction is carried out at 140°–180° F. Above 200° F. the viscosity increases again. Upon addition the mixture should be stirred and the heating continued until the polyester material is completely dissolved. With a concentration of sulfuric acid of about 95% by weight and a temperature of about 140° to 200° F. this will take about 3 to 5 minutes. Upon dissolution of the polyester material a relatively syrupy mixture is provided.

Where the polyester contains no pigments or dyes it thereafter is added to water. Almost instantaneously terephthalic acid will be precipitated. The quantity of water is not critical. It has been found that about 4–10 parts by weight of water per part of polyester material should be used.

In most instances the polyester starting material will contain dyes and pigments. In order to remove such dyes and pigments it has been found that a two step removal treatment can be used. This method comprises adding the polyester-sulfuric acid mixture to water which has been made alkaline with, for example, sodium hydroxide. The alkalinity of the water is controlled so that any residual sulfuric acid and all of the terephthalic acid is neutralized. In this way the components of the reaction mixture to be reclaimed remain in solution and a substantial amount of the pigments and/or dyes, being insoluble, precipitate and thereafter may be recovered by filtration. In the second step, to remove the remaining pigments and/or dyes, the filtrate, containing the dissolved components to be recovered, is passed through an ion exchange column. Alternatively, the filtrate can be mixed with clay or charcoal to remove such materials. The clear, colorless liquid remaining after the removal of the dyes and pigments contains, in the case of a terephthalic acid-ethylene glycol polymer starting material, sodium terephthalate, ethylene glycol, sodium sulfate, and sodium hydroxide. To reclaim the former two the following steps are employed. The mixture is agitated and a quantity of sulfuric acid or other acid, for example, citric or hydrochloric, is added so that the pH of the solution is reduced to about 2.5–3.0. The sodium terephthalate is converted to insoluble terephthalic acid which precipitates as a white crystalline material. The terephthalic acid is then recovered, washed, and dried. It has a purity of 99+% and is of fiber grade.

The remaining filtrate is mixed, using intensive agitation, with suitable organic solvent in which the ethylene glycol is soluble. Such a solvent is trichloroethylene. As a result two phases are formed, water and organic. The two are separated, a separation that is readily effected, and the organic phase distilled to recover ethylene glycol and trichloroethylene. The latter may be reused in the process; the former reused for conventional purposes.

An alternative method for recovering the ethylene glycol comprises treating the filtrate with sodium hydroxide. The quantity added is sufficient to raise the pH of the mixture to about 6.7 to 7.5. To this mixture is added sodium sulfate in an amount sufficient to form a saturated solution. Afterwards, the ethylene glycol is "salted out" and rises to the top of the solution. It can then be decanted off and reused.

In the first method disclosed for recovering the glycol, the water phase left after the organic phase has been removed, is treated by adding thereto, with agitation, lime in an amount stoichiometrically equal to the sodium sulfate and sulfuric acid present in the water. Calcium sulfate precipitates, and is recovered by filtration or by centrifuging. The remaining liquid, comprising primarily water and sodium hydroxide, may be reused in the process.

Having thus described the present invention several specific examples of it will be presented and compared with various prior art and/or inoperative examples. Example VIII constitutes as of this date the preferred example of the present invention.

EXAMPLE I

To a beaker containing 100 parts by weight of sulfuric acid having a concentration of 50% acid and 50% water and heated to about 212° F. were added 100 parts by weight of scrap cuttings of a polyester fabric of the terephthalic acid-ethylene glycol type. This type fabric was also employed in the subsequent examples. The polyester scrap-sulfuric acid mixture was maintained at about 212° F. for about 5 days and the polyester scrap thereafter removed and examined. No discernable depolymerization or degradation of the fabric had occurred. The liquid remaining in the beaker was poured into another beaker containing about 200 parts by weight of cold water. No precipitate of terephthalic acid formed.

EXAMPLE II

Substantially the foregoing procedure was followed except that the concentration of sulfuric acid was increased to 70% (70% acid–30% water). Again no precipitate of terephthalic acid was produced.

EXAMPLE III

Substantially the same procedure as before was followed except that an 86% sulfuric acid solution (86% acid–14% water) was utilized. After 2 days of treatment a slight dissolving or depolymerization of the polyester was noted. At that point the liquid in the beaker was poured into cold water and a minor amount or terephthalic acid was precipitated.

EXAMPLE IV

The foregoing procedures were repeated except an 87% sulfuric acid solution (87% acid–13% water) was utilized and a temperature of 175° F. was employed. After five minutes of this treatment the polyester fabric had all dissolved and only a syrupy mixture remained. This was poured into the cold water and a precipitate immediately formed. Upon analysis it was determined that the precipitate was terephthalic acid. The acid was separated, weighed and analyzed for purity. It was found to be of high purity. Substantially all of the terephthalic acid believed to be present in the polymer was recovered.

EXAMPLES V AND VI

The procedure of Example IV was repeated using concentrations of 92% and 95%, respectively. Results substantially similar to Example IV were obtained.

EXAMPLE VII

The procedure of Example IV was repeated except that 40 parts by weight of 95% sulfuric acid and 60 parts by weight of polyester fabric were utilized. After a very slight dissolving of the fabric had occurred.

EXAMPLE VIII

The preferred embodiment of the present invention is most easily understood by referring to the flow diagram.

Into a conventional mixer, equipped with heating means and mixing means, was introduced concentrated sulfuric acid to a quantity of 200 parts by weight. Heat was added until the acid reached a temperature of 150° F. The mixing means was begun, and scrap polyester cuttings (a terephthalic acid-ethylene glycol polymer) of various sizes, colors and textures (weaves, knits, etc.) were added to a quantity of 100 parts by weight. After 3 to 5 minutes of mixing, a smooth syrupy fluid was obtained. This fluid was then pumped to a tank, equipped with suitable mixing means, containing an aqueous alkali mixture consisting of about 4–10 parts by weight water (per part of polyester material) and about 180 to 250 parts by weight of sodium hydroxide (per part of polyester material). The quantity of sodium hydroxide was sufficient to not only neutralize the sulfuric acid in the acid-polyester fluid, but to also neutralize the terephthalic acid.

As the acid-polyester fluid was pumped into the agitated dilute alkali water tank, the acid-polyester underwent an instantaneous depolymerization and the acids produced were converted to sodium terephthalate and sodium sulfate. After 3–5 minutes of intensive mixing of the mixture there was present in the tank, at a temperature of around 120°–150° F., a deeply colored solution containing a small percentage of insoluble material. It was found experimentally that the insoluble fraction comprised about 4% on the average of the feed polyester scrap material. This agrees with the weight present in the feed material of pigments, dyes, fiber surface treatments for dye receptivity, etc.

The insoluble material was then filtered off by conventional means, and discarded. The filtrate, at a pH of about 7.5–9.0, was a dark colored but clear liquid containing sodium sulfate, glycol, sodium terephthalate and a small amount of sodium hydroxide. The liquid was then clarified by passing it through an ion exchange column. The dissolved sodium terephthalate, glycol, and sodium sulfate passed through the color removal column, and emerged as a clear almost colorless solution. This solution was pumped into a suitable container equipped with intensive agitation means. Here sulfuric acid was added until the pH of the solution was reduced from 7.5–9.0 to 2.5–3.0. The soluble sodium terephthalate was converted to insoluble terephthalic acid, and precipitated as a white crystalline precipitate. The terephthalic acid was removed in a continuous solid bowl centrifuge, and also washed in the centrifuge to remove any entrained sulfuric acid, the washings being neutralized by limestone and sewered.

After drying in a conventional dryer, the terephthalic acid was found to be a pure white powder, of 99+% purity, with less than 0.2% ash. It was also found to be very low in cobalt, manganese, bromine or other contaminating ions. In short, it was what is known in the art as fiber grade.

The mother liquor from the centrifuge step was then pumped to a contactor. This was of conventional design with a chamber equipped with intensive agitation means where the solution was mixed with trichloroethylene. Other suitable organic solvents could be employed. Here, a portion of the glycol dissolved in the organic solvent. The two phases, water and organic, were separated, and the organic phase sent to a conventional still to separate the glycol from the organic solvent. If desired, the recovered solvent can be reused in a subsequent glycol separation step. Any glycol not picked up by the solvent continues to recirculate in the system until it is ultimately picked up by the solvent.

The water phase from the stripper separator was pumped to a tank equipped with an agitator. Here lime was added in an amount stoichiometrically equal to the sodium sulfate and sulfuric acid present in the water. Calcium sulfate formed as an insoluble precipitate and was filtered off, and the sodium hydroxide and excess water mixture was returned to the point in the process where the acid-polyester fluid was treated with caustic-water.

There are, of course, several variations of the process, primarily as a result of the choice of scrap feed for the reaction. For example, if what is known as mill waste is used one decolorizing step may be eliminated. This scrap is from the extrusion of the fiber, and contains no dyes or treatments, so there is no need for a decolorization step. The initial filtration of the insoluble portion leaves only a delustrant pigment residue of less than 1%. The terephthalic acid from this scrap however is indistinguishable from the acid obtained from the multiple colored cutting scrap. Such is the efficiency of the process.

The purity of the glycol after distillation is of the order of 99+% and is suitable for use in polymerization again. Over all, reaction efficiency shows a yield of between 80 and 83 gms. T.P.A. per 100 gms. polyester cuttings, and 28-31 gms. glycol per 100 gms. cuttings. This agrees very closely with a theoretical yield of a total of 119 gms. of T.P.A. plus glycol per 100 gms. of cuttings.

Having thus described our invention, we claim:

1. A method for recovering terephthalic acid from a polyester material produced from two or more monomers, one of which is terephthalic acid comprising
   A. adding said polyester material to concentrated sulfuric acid heated to a temperature of about 140° F. to 200° F., said concentrated sulfuric acid comprising at least about 87% by weight of sulfuric acid, and the weight of concentrated sulfuric acid is at least as great as the amount of polyester material,
   B. adding said polyester material-sulfuric acid mixture to water wherein said terephthalic acid precipitates, and
   C. separating terephthalic acid from said mixture.

2. A method for recovering terephthalic acid from a polyester material containing as one monomer terephthalic acid comprising:
   A. adding said polyester material to a concentrated sulfuric acid heated to a temperature of about 140° to 200° F., said concentrated sulfuric acid comprising at least about 87% by weight of sulfuric acid,
   B. adding said polyester material-sulfuric acid mixture to an alkali water mixture, the amount of alkali contained in said mixture being sufficient to neutralize any remaining sulfuric acid and the terephthalic acid produced from the reaction of the sulfuric acid with the polyester material,
   C. separating from the mixture of step (B) any insoluble materials,
   D. adding an acid to the solution from step (C) to precipitate terephthalic acid, the amount of said acid added being sufficient to provide a solution having a pH of about 2.5 to 3, and
   E. removing said precipitated terephthalic acid.

3. The method of claim 2 wherein the weight of concentrated sulfuric acid is at least as great as the amount of polyester material.

4. The method of claim 3 wherein said concentrated sulfuric acid is agitated and said polyester material is allowed to remain in said agitated sulfuric acid for a period of time from about 3 to 5 minutes.

5. The method of claim 2 wherein after step (C) and before step (D) the solution is subjected to a decolorizing step.

6. The method of claim 5 wherein said polyester material is produced from two or more monomers, one being ethylene glycol and another being terephthalic acid, and wherein said ethylene glycol is recovered.

7. The method of claim 6 wherein said ethylene glycol is recovered by subjecting the solution from step (D) to the following steps
   F. adding to the solution an organic solvent in which said ethylene glycol is soluble, and
   G. separating said organic solvent from said ethylene glycol, and
   H. distilling ethylene glycol from said solvent.

8. The method of claim 1 wherein said sulfuric acid comprises about 95% by weight of sulfuric acid.

9. The method of claim 8 wherein the weight of concentrated sulfuric acid is at least 60% by weight of said mixture of said concentrated acid and said polyester material.

* * * * *

UNITED STATES PATENT AND TRADEMARK OFFICE
CERTIFICATE OF CORRECTION

PATENT NO. : 3,952,053
DATED : April 20, 1976
INVENTOR(S) : George E. Brown, Jr. and Richard C. O'Brien It is certified that error appears in the above-identified patent and that said Letters Patent are hereby corrected as shown below:

Column 1, line 37, delete "processes" and insert --a--.

Column 2, line 8, "acidethylene" should be --acid-ethylene--.

Column 3, line 16, "in" should be --is--.

Column 5, line 67, after "After" insert --5 minutes--.

Signed and Sealed this

Twenty-eighth Day of September 1976

[SEAL]

Attest:

RUTH C. MASON
Attesting Officer

C. MARSHALL DANN
Commissioner of Patents and Trademarks